United States Patent
Park et al.

(10) Patent No.: US 12,171,584 B2
(45) Date of Patent: Dec. 24, 2024

(54) APPARATUS AND METHOD FOR ESTIMATING BODY COMPONENT

(71) Applicant: SAMSUNG ELECTRONICS CO., LTD., Suwon-si (KR)

(72) Inventors: Yun S Park, Suwon-si (KR); June Young Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 789 days.

(21) Appl. No.: 17/320,434

(22) Filed: May 14, 2021

(65) Prior Publication Data

US 2022/0233149 A1 Jul. 28, 2022

(30) Foreign Application Priority Data

Jan. 25, 2021 (KR) .................. 10-2021-0010250

(51) Int. Cl.
*A61B 5/00* (2006.01)
*A61B 5/1477* (2006.01)
(Continued)

(52) U.S. Cl.
CPC .......... *A61B 5/7246* (2013.01); *A61B 5/0075* (2013.01); *A61B 5/1477* (2013.01); *A61B 5/1495* (2013.01); *G06N 20/10* (2019.01)

(58) Field of Classification Search
CPC ............. A61B 5/0075; A61B 5/14532; A61B 5/14546; A61B 5/1455; A61B 5/1477;
(Continued)

(56) References Cited

U.S. PATENT DOCUMENTS

| 5,957,841 A | 9/1999 | Maruo et al. |
| 6,574,490 B2 | 6/2003 | Abbink et al. |

(Continued)

FOREIGN PATENT DOCUMENTS

| JP | 2010-528744 A | 8/2010 |
| JP | 5673823 B2 | 1/2015 |

(Continued)

OTHER PUBLICATIONS

Bai, Chuannan, "Noninvasive Near Infrared Spectroscopy on Living Tissue With Miltivariate Calibration Approaches," Ph.D. Thesis, Graduate College The University of Iowa, Iowa City, Iowa, Dec. 2010, (207 pages).

(Continued)

*Primary Examiner* — Eric F Winakur
*Assistant Examiner* — Abel Seifu Abegaz
(74) *Attorney, Agent, or Firm* — Sughrue Mion, PLLC

(57) ABSTRACT

An apparatus and a method for estimating a body component are provided. According to an example embodiment, the apparatus for estimating a body component includes: a sensor configured to obtain, from an object of a user, a first spectrum in a first concentration period of a body component and a second spectrum in a second concentration period of the body component; and a processor configured to extract a first feature vector based on the first spectrum and the second spectrum, to extract a second feature vector based on a standard spectrum and the second spectrum, and to perform first calibration by generating an estimation model for estimating the body component, generation of the estimation model being based on a similarity between the first feature vector and the second feature vector.

17 Claims, 16 Drawing Sheets

(51) Int. Cl.
*A61B 5/1495* (2006.01)
*G06N 20/10* (2019.01)

(58) Field of Classification Search
CPC ... A61B 5/1495; A61B 5/7235; A61B 5/7246; A61B 2560/0223; G06N 20/10
See application file for complete search history.

(56) References Cited

U.S. PATENT DOCUMENTS

| | | | |
|---|---|---|---|
| 7,460,895 | B2 | 12/2008 | Arnold et al. |
| 2001/0021803 | A1 | 9/2001 | Blank et al. |
| 2006/0167348 | A1* | 7/2006 | Arnold ............... G01N 21/35 356/300 |
| 2009/0054740 | A1 | 2/2009 | Gudmundsson et al. |
| 2010/0168533 | A1 | 7/2010 | Johnsen et al. |
| 2013/0204102 | A1 | 8/2013 | Sen et al. |
| 2016/0139041 | A1 | 5/2016 | Gulati et al. |
| 2018/0028097 | A1* | 2/2018 | Chang ............... G01N 21/359 |
| 2019/0069821 | A1* | 3/2019 | Segman ............. G01N 21/359 |
| 2019/0117136 | A1 | 4/2019 | Lee et al. |
| 2019/0166030 | A1 | 5/2019 | Chen et al. |
| 2019/0261928 | A1 | 8/2019 | Jos et al. |

FOREIGN PATENT DOCUMENTS

| | | |
|---|---|---|
| KR | 10-0268968 B1 | 12/2000 |
| KR | 10-2019-0043967 A | 4/2019 |
| KR | 10-2019-0101867 A | 9/2019 |

OTHER PUBLICATIONS

Maruo et al., "Near-infrared noninvasive blood glucose prediction without using multivariate analyses: introduction of imaginary spectra due to scattering change in the skin," Journal of Biomedical Optics, vol. 20(4), 047003, SPIE, Apr. 2015, (12 pages).

Jintao et al., "Noninvasive and fast measurement of blood glucose in vivo by near infrared (NIR) spectroscopy," Elsevier, Spectrochimica Acta Part A:Molecular and Bimolecular Spectroscopy 179, Feb. 16, 2017, pp. 250-254 (6 total pages).

Olesberg et al., "In Vivo Near-Infrared Spectroscopy of Rat Skin Tissue with Varying Blood Glucose Levels," Analytical Chemistry, ACS Publications, American Chemical Society, 78, 1, Nov. 30, 2005, (8 pages).

Ferre et al., "Net analyte signal calculation for multivariate calibration," Elsevier, Chemometrics and intelligent laboratory systems 69, Jul. 11, 2003, pp. 123-136, (14 pages).

Haenlein et al., "A Beginner's Guide to Partial Least Squares Analysis," Lawrence Erlbaum Associates, Inc. Understanding Statistics, 3(4), Nov. 2004, pp. 283-297, (16 total pages).

* cited by examiner

APPARATUS AND METHOD FOR ESTIMATING BODY COMPONENT

CROSS-REFERENCE TO RELATED APPLICATION(S)

This application claims priority from Korean Patent Application No. 10-2021-0010250, filed on Jan. 25, 2021, in the Korean Intellectual Property Office, the entire disclosure of which is herein incorporated by reference for all purposes.

BACKGROUND

1. Field

Example embodiments of the disclosure relate to an apparatus and a method for non-invasively detecting a body component.

2. Description of the Related Art

Recently, with the aging population, soaring medical costs, and a lack of medical personnel for specialized medical services, research is being actively conducted on information technology (IT)-medical convergence technologies, in which IT technology and medical technology are combined. Particularly, monitoring of the health condition of the human body is not limited to places such as hospitals, but is expanding to mobile healthcare fields that may monitor a user's health condition anywhere and anytime in daily life, e.g., at home or office.

SUMMARY

According to an aspect of an example embodiment, provided is an apparatus for estimating a body component, the apparatus including: a sensor configured to obtain, from an object of a user, a first spectrum in a first concentration period of a body component and a second spectrum in a second concentration period of the body component; and a processor configured to extract a first feature vector based on the first spectrum and the second spectrum, to extract a second feature vector based on a standard spectrum and the second spectrum, and to perform first calibration by generating an estimation model for estimating the body component, generation of the estimation model being based on a similarity between the first feature vector and the second feature vector.

The similarity may include a cosine similarity.

The first concentration period may be a relatively high concentration period compared to the second concentration period; and the second concentration period may include a period in which the user is in a fasting state.

By variously setting a number of principal components, the processor may be further configured to extract the first feature vector and the second feature vector according to each set number of principal components, determine an optimal number of principal components based on the similarity between the extracted first feature vector and the second feature vector according to each set number of principal components, and generate the estimation model based on the determined optimal number of principal components.

The processor may be further configured to determine, as the optimal number, a set number of principal components at which the similarity between the first feature vector and the second feature vector has a maximum value.

The processor may be further configured to, based on the determined optimal number of principal components, generate the estimation model by applying at least one analysis algorithm among net analyte signal (NAS), classical least squares (CLS), partial least squares (PLS), Lasso, Neural network, and support, vector machine (SVM).

The processor may be further configured to estimate the body component based on a third spectrum, obtained after the first calibration, and the generated estimation model.

The processor may be further configured to extract a third feature vector based on the third spectrum and the second spectrum, and the processor is further configured to, based on a similarity between the third feature vector and the second feature vector being less than a predetermined threshold, perform second calibration.

The body component may include at least one of blood glucose, cholesterol, triglyceride, protein, lactate, antioxidant, ethanol, carotenoid, urea, and uric acid.

According to an aspect of an example embodiment, provided is an apparatus for estimating a body component, the apparatus including: a sensor configured to obtain, from an object of a user, a first spectrum in a first concentration period of a body component and a second spectrum in a second concentration period of the body component; and a processor configured to extract a first feature vector based on a spectrum of the first concentration period and the second spectrum, to extract a second feature vector based on a standard spectrum and the second spectrum, and to determine at least one of an analysis algorithm or a measurement position of the object based on a similarity between the first feature vector and the second feature vector.

The processor may be further configured to, based on the similarity being greater than or equal to a predetermined threshold, determine a net analyte signal (NAS) algorithm as the analysis algorithm, or based on the similarity being less than the predetermined threshold, determine any one of classical least squares (CLS), partial least squares (PLS), Lasso, Neural network, and support vector machine (SVM) as the analysis algorithm.

The processor may be further configured to, based on the similarity being less than a predetermined threshold, control to guide the user to change the measurement position of the object, at which the first spectrum is to be re-obtained.

The processor may be further configured to control to guide the user to change the measurement position of the object, based on a measurement position database including information on a plurality of measurement positions of each user.

The measurement position database may include at least any one of a list of a plurality of measurement positions associated with a type of a body component to be estimated, a priority of the plurality of measurement positions, and an optimal measurement position of each user.

According to an aspect of an example embodiment, provided is a method of estimating a body component, the method including: obtaining, from an object of a user, a first spectrum measured in a first concentration period of a body component and a second spectrum in a second concentration period of the body component; extracting a first feature vector based on the first spectrum and the second spectrum; extracting a second feature vector based on a standard spectrum and a spectrum of the second spectrum; and performing first calibration by generating an estimation model for estimating the body component, generation of the estimation model being based on a similarity between the first feature vector and the second feature vector.

The method may further include: variously setting a number of principal components, and extracting the first feature vector and the second feature vector according to each set number of principal components; determining an optimal number of principal components based on the similarity between the extracted first feature vector and the second feature vector according to each set number of principal components; and generating the estimation model based on the determined optimal number of principal components.

The determining the optimal number of principal components may include determining, as the optimal number, a set number of principal components at which the similarity between the first feature vector and the second feature vector has a maximum value.

The generating the estimation model based on the determined optimal number of principal components may include generating the estimation model by applying at least one analysis algorithm among net analyte signal (NAS), classical least squares (CLS), partial least squares (PLS), Lasso, Neural network, and support vector machine (SVM).

The method may further include estimating the body component based on a third spectrum, obtained after the first calibration, and the generated estimation model.

The method may further include extracting a third feature vector based on the third spectrum and the second spectrum; and based on a similarity between the third feature vector and the second feature vector being less than a predetermined threshold, performing second calibration.

BRIEF DESCRIPTION OF THE DRAWINGS

The above and/or other will be more apparent from the following detailed description of exemplary embodiments taken in conjunction with the accompanying drawings.

DETAILED DESCRIPTION

Figure 1:
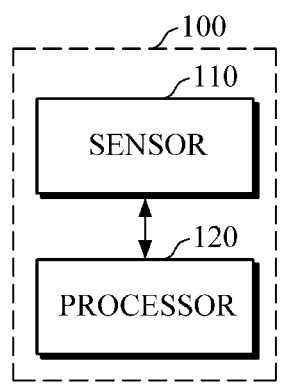
FIG. 1 is a block diagram illustrating an apparatus for estimating a body component according to an example embodiment of the disclosure.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, example embodiments of an apparatus and method for estimating a body component will be described in detail with reference to the accompanying drawings.

FIG. 1 is a block diagram illustrating an apparatus for estimating a body component according to an example embodiment.

Various embodiments of the apparatus 100 for estimating a body component may be mounted in a terminal, such as a smartphone, a tablet personal computer (PC), a desk top computer, a laptop computer, a wearable device, and the like. The wearable device may be implemented as a wristwatch-type wearable device, a bracelet-type wearable device, a wristband-type wearable device, a ring-type wearable device, a glasses-type wearable device, a headband-type wearable device, or the like, but the wearable device is not limited thereto. For example, the wearable device may be mounted in hardware manufactured in various types for use in a specialized medical institution.

Referring to FIG. 1, the apparatus 100 for estimating a body component includes a sensor 110 and a processor 120.

The sensor 110 may estimate a body component from a user's object and/or may obtain a spectrum for calibration. The object may be, for example, an area on a wrist which is adjacent to a radial artery, or an upper portion of the wrist where veins or capillaries are located. Alternatively, the object may be a peripheral part of the body, such as fingers, toes, and the like, where blood vessels are densely distributed.

The sensor 110 may include a light source emitting light onto an object, and a detector obtaining a spectrum by detecting light emanating from body tissue after the light, emitted onto the object by the light source, is scattered or reflected from the body tissue of the object. The light source may be formed as a multi-wavelength (e.g., green wavelength, blue wavelength, red wavelength, infrared wavelength, etc.) light source array of light sources configured to emit light of a plurality of different wavelengths. However, the light source is not limited thereto, and the light source or the detector may include a filter for passing light of different wavelengths. The light source may include at least one of a light emitting diode (LED), a laser diode (LD), a phosphor, etc., but is not limited thereto. The detector may include a photodiode, a photo transistor (PTr), an image sensor (e.g., complementary metal-oxide semiconductor (CMOS) image sensor), or a spectrometer for detecting a spectrum having a relatively broadband wavelength, etc., but is not limited thereto.

For example, the sensor 110 may obtain a first spectrum in a first concentration period. The first concentration period may be a range after a user ingests food containing a body component to be estimated, and may refer to a relatively high concentration period of the body component.

Further, the sensor 110 may obtain a second spectrum in a second concentration period of the body component. The second concentration period may be a relatively low concentration period of the body component, and may be, for example, a period in which a user is in a fasting state.

The processor 120 may perform calibration for estimating a body component based on the obtained first and second spectra. For example, the processor 120 may generate a body component estimation model based on the first spectrum and the second spectrum, which are obtained in different concentration periods, and a pre-obtained standard spectrum. The standard spectrum may refer to a spectrum previously obtained using a standard sample containing no body component.

For example, the processor 120 may extract a first feature vector based on the first spectrum and the second spectrum, and may extract a second feature vector based on the standard spectrum and the second spectrum. In addition, the processor 120 may generate an estimation model by using the first feature vector and the second feature vector. The first feature vector and the second feature vector may include a net analyte signal (NAS) vector, but are not limited thereto.

The processor 120 may calculate a similarity between the first feature vector and the second feature vector, and may generate an estimation model based on the calculated similarity. The similarity may include a cosine similarity but is not limited thereto. The cosine similarity may be calculated, as represented by the following Equation 1.

$$\cos\theta = \frac{V_1 \cdot V_2}{|V_1||V_2|} \quad \text{[Equation 1]}$$

Herein, $V_1$ and $V_2$ denote the first feature vector and the second feature vector, respectively; and the cosine similarity value denotes a value obtained by dividing an inner product between the first and second feature vectors by a value obtained by multiplying magnitudes of the first and second feature vectors.

By varying a number of principal components, the processor 120 may extract the first feature vector and the second feature vector according to each number of principal components, and may calculate a similarity between the first feature vector and the second feature vector according to each number of principal components. In other words, the processor 120 may set the number of principal components to various numbers, and extract the first feature vector and the second feature vector with respect to each of the various numbers of principal components. The processor 120 may determine an optimal number of principal components based on the similarity for each number of principal components. The processor 120 may determine, as the optimal number, a number of principal components having a maximum similarity value, among the similarities for each number of principal components. The processor 120 may generate an estimation model by using the determined optimal number of principal components.

Based on the determined optimal number of principal components, the processor 120 may generate an estimation model by applying at least one analysis algorithm among net analyte signal (NAS), classical least squares (CLS), partial least squares (PLS), Lasso, Neural network, and support vector machine (SVM).

In another example, by performing calibration, the processor 120 may determine an analysis algorithm for generating a body component estimation model.

For example, by using a predetermined number of principal components, the processor 120 may extract the first feature vector and the second feature vector from the first spectrum, the second spectrum, and the standard spectrum, and may calculate a similarity between the first feature vector and the second feature vector. In addition, if the calculated similarity is greater than or equal to a predetermined threshold, the processor 120 may determine, for example, an net analyte signal (NAS) algorithm, as an analysis algorithm; and if the calculated similarity is less than the predetermined threshold, the processor 120 may determine, for example, any one of classical least squares (CLS), partial least squares (PLS), Lasso, Neural network, and support vector machine (SVM), as an analysis algorithm.

Upon determining the analysis algorithm, the processor 120 may generate an estimation model by using the determined analysis algorithm.

In yet another example, by performing calibration, the processor 120 may construct a database of a plurality of measurement positions for each user and/or may determine an optimal measurement position of an object.

A user's skin has different tones, structures, and substances according to its positions, and thus has different optical characteristics. With respect to a body component to be estimated, the processor 120 may construct a database, including a list of a plurality of measurement positions, a priority of the plurality of measurement positions, and an optimal measurement position, for each user.

In this case, the list of the plurality of measurement positions may be determined to be various parts of the body, such as an upper portion of the wrist, fingers, toes, ears, and the like; and may include positions at which the apparatus for estimating a body component is worn or carried, a list of predetermined measurement positions associated with a type of a body component to be estimated, or measurement positions determined according to a user's request.

In addition, the priority of the plurality of measurement positions may be determined based on the above similarity. For example, by extracting the first feature vector and the second feature vector from the first spectrum, the second spectrum, and the standard spectrum at the respective measurement positions in the list of the plurality of measurement positions, the processor 120 may calculate a similarity between the first feature vector and the second feature vector, and may determine a priority based on a ranking of similarities at the respective measurement positions (e.g., determine a higher priority for a higher highest similarity). Alternatively, a priority of the plurality of measurement positions may be determined by a user's selection.

In addition, the processor 120 may determine, as a user's optimal measurement position, a measurement position having a maximum similarity value among the similarities at the respective measurement positions. Alternatively, upon providing a user with each similarity and priority at the plurality of measurement positions through a display module and the like, the processor 120 may determine a measurement position, designated by the user, as the optimal measurement position.

Upon receiving a request for estimating a body component, the processor 120 may control the sensor 110 to obtain a third spectrum for estimating a body component, and may estimate a body component based on the third spectrum, obtained at an estimation time, and the generated estimation model. The body component that is estimated may include any, one of blood glucose, cholesterol, triglyceride, protein, lactate, antioxidant, ethanol, carotenoid, urea, and uric acid, but is not limited thereto.

Upon obtaining the third spectrum, the processor 120 may determine whether to again perform calibration before, after, or simultaneously with estimation of a body component. For example, the processor 120 may extract a third feature vector based on the third spectrum and the second spectrum as described above, may calculate a similarity by using the second feature vector, obtained based on the second spectrum and the standard spectrum as described above, and the third feature vector; and if the calculated similarity is less than a predetermined threshold, the processor 120 may perform the calibration again. In this case, the processor 120 determines whether to perform the calibration again by using the second spectrum, the third spectrum, and the standard spectrum, rather than using data measured for a long period of time, thereby determining, in real time, accuracy in estimating a body component according to a set number of principal components.

In addition, upon obtaining the third spectrum, the processor 120 may determine whether to change a current measurement position before, after, or simultaneously with estimation of the body component, and if it is required to change the measurement position, the processor 120 may control to guide a user on a changed measurement position.

For example, the processor 120 may calculate a similarity by using the second feature vector and the third feature vector as described above; and if the calculated similarity is less than a predetermined threshold, the processor 120 may control to guide a user to change a measurement position. In this case, the processor 120 may provide information for guiding a user to change a measurement position by using, for example, a display module or an audio output module mounted in the apparatus 100 for estimating a body component or in a connected external device.

The processor 120 may control to guide a user to change a measurement position of an object based on the constructed database of measurement positions for each user. In this case, based on the determined priority of the plurality of measurement positions, the processor 120 may control to guide a measurement position to be changed, or by providing the similarity and priority at each position along with the list of the plurality of measurement positions, the processor 120 may allow a user to designate a measurement position. After the measurement position is changed, the sensor 110 may re-obtain the first spectrum or obtain the third spectrum based on the changed measurement position.

If a similarity between the second feature vector and the third feature vector is greater than or equal to a predetermined threshold, the processor 120 may estimate a body component by using the third spectrum measured at a corresponding measurement position.

In an example embodiment, without a need to measure spectra for a long period of time to estimate a body component, a body component may be estimated in real time by obtaining spectra in a low concentration period and spectra in a high concentration period. Also, in an example embodiment, the body component may be estimated with a higher accuracy without a need to measure spectra for a long period of time to estimate the body component.

Figure 2:
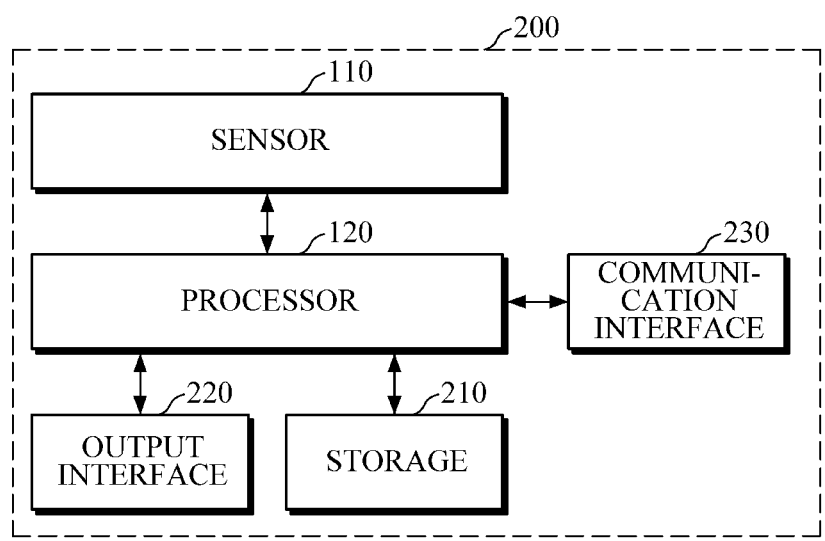
FIG. 2 is a block diagram illustrating an apparatus for estimating a body component according to another example embodiment of the disclosure.

FIG. 2 is a block diagram illustrating an apparatus for estimating a body component according to another example embodiment.

Referring to FIG. 2, the apparatus 200 for estimating a body component includes the sensor 110, the processor 120, a communicator (or communication interface) 230, an outputter (or output interface) 220, and a storage 210.

As described above, the sensor 110 may estimate a body component from a user's object and/or may obtain spectra for calibration. In an example embodiment, the sensor 110 may be omitted as will be described later.

The communicator 230 may, be connected to an external device using one or more of communication techniques under the control of the processor 120, and may receive the first spectrum, the second spectrum, and the standard spectrum from the external device. In this case, the external device may include one or more of various devices for measuring and/or managing spectra, such as a smartphone, a tablet PC, a wearable device, or an external device for measuring spectra, etc., with no particular limitation. In addition, the communicator 230 may transmit a processing result of the processor 120 to the external device.

Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, and mobile communication, but are not limited thereto.

In the case where both the sensor 110 and the communicator 230 are mounted in the apparatus 200 for estimating a body component, the processor 120 may selectively control the sensor 110 and the communicator 230 to obtain the first spectrum and the second spectrum. The outputter 220 may output a processing result of the processor 120 and may provide the output processing result for a user. The outputter 220 may provide the information for the user by using one or more of various visual and/or non-visual methods using a display module, a speaker, a haptic device, etc., mounted in the apparatus 200 for estimating a body component.

For example, the outputter 220 may visually display an estimated body component value of a user by using various methods, such as by changing color, line thickness, font, and the like based on whether the estimated body component value falls within or outside a normal range. In addition, along with the visual display, the outputter 220 may provide the information using vibrations, tactile sensation, and the like according to whether the estimated body component value is abnormal, so that the user may easily recognize abnormality. Alternatively, upon comparing the estimated body component value with a previous estimation history, if it is determined that the estimated body component value is abnormal, the outputter 220 may provide a warning message, an alarm signal, etc., as well as information on a user's action such as food information that the user should be careful about or related hospital or doctor's information.

In another example, the outputter 220 may provide guide information when the processor 120 guides a user to change a measurement position of the object. In this case, based on priority of the plurality of measurement positions in the measurement position database of each user, the outputter 220 may display a measurement position to be changed by using various visual/non-visual methods, or may provide the similarity or priority at each position along with the list of the plurality of measurement positions.

The storage 210 may store a variety of reference information used for estimating a body component, and information such as the obtained first and second spectra, the standard spectrum, the estimated body component value, and the like. The reference information may include user information such as a user's age, sex, occupation, current health condition, and the like, but is not limited thereto. The storage 210 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

FIGS. 3A to 3F are diagrams explaining an example of determining an optimal number of principal components based on a similarity between the first feature vector and the second feature vector according to different numbers of principal components, according to an example embodiment.

Figure 3A:
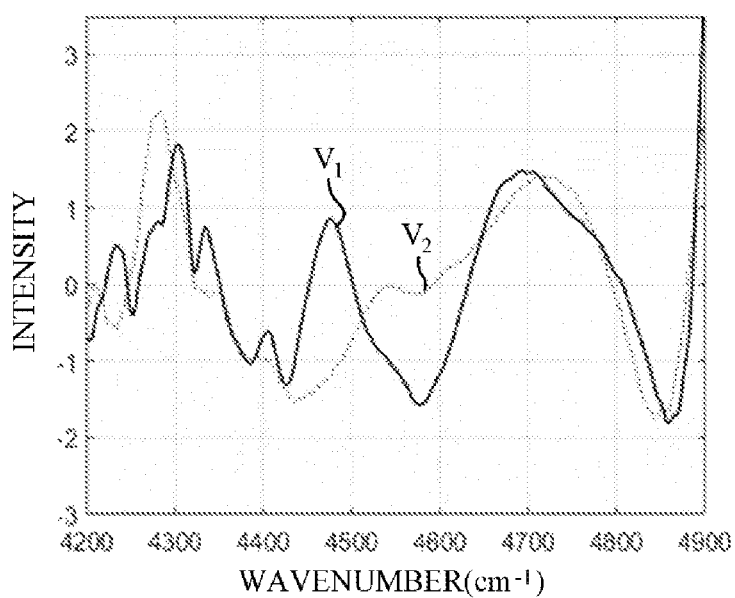
FIGS. 3A to 3F are diagrams explaining an example of determining an optimal number of principal components according to an example embodiment.
Figure 3B:
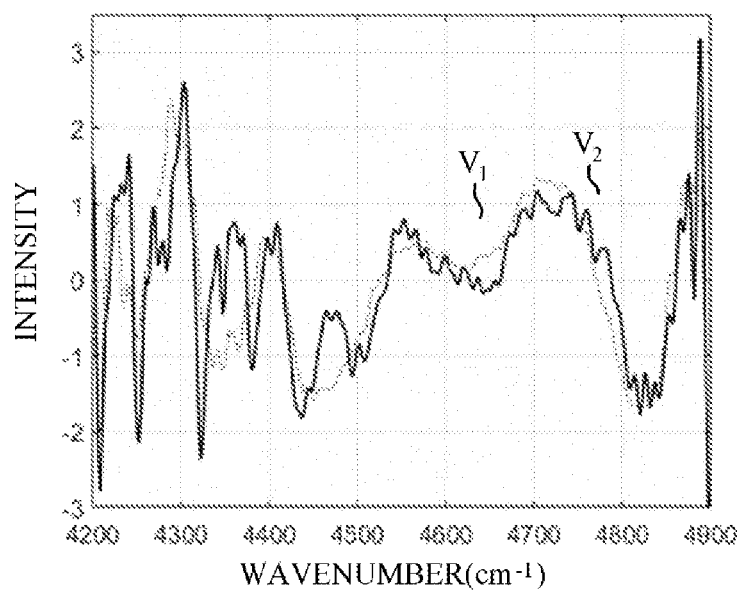
Figure 3C:
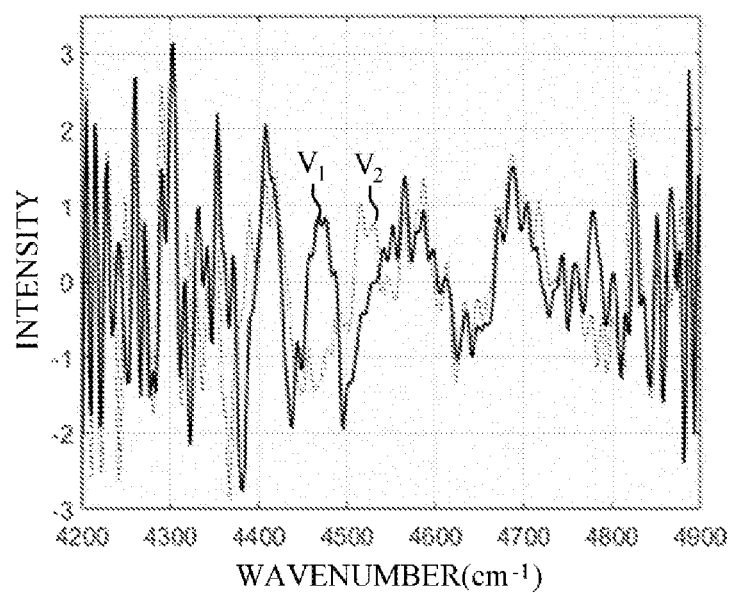
Figure 3D:
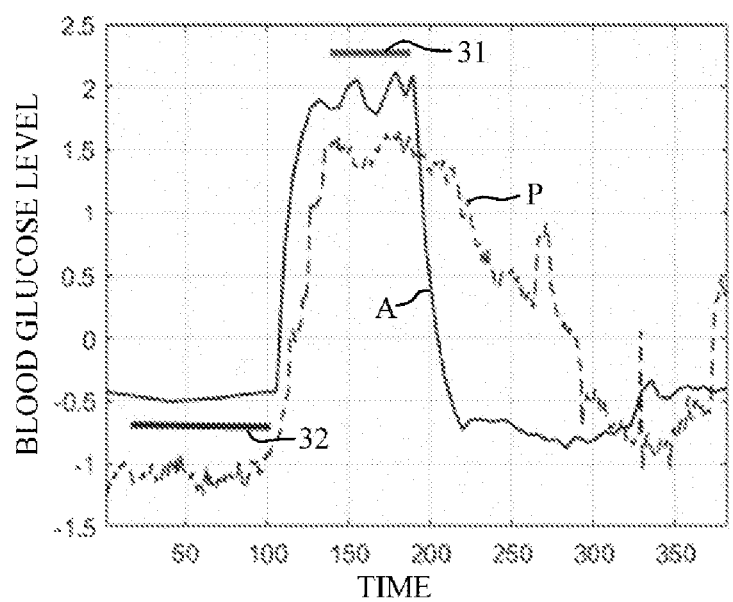
Figure 3E:
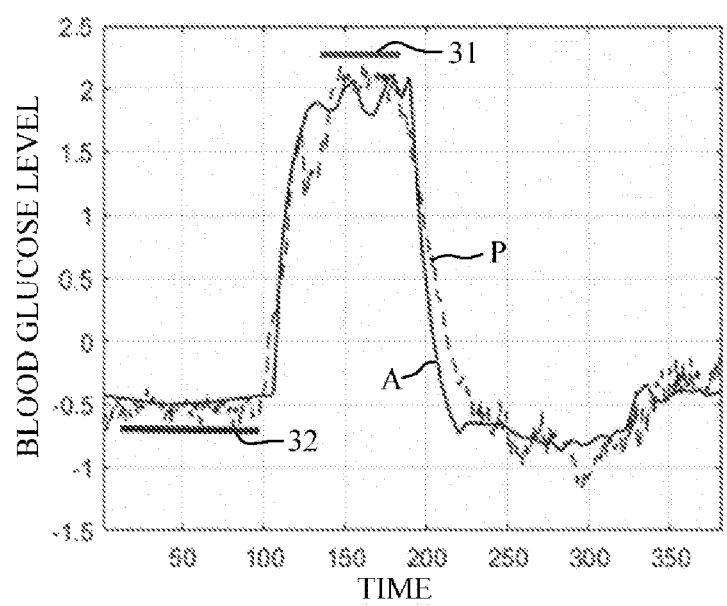
Figure 3F:
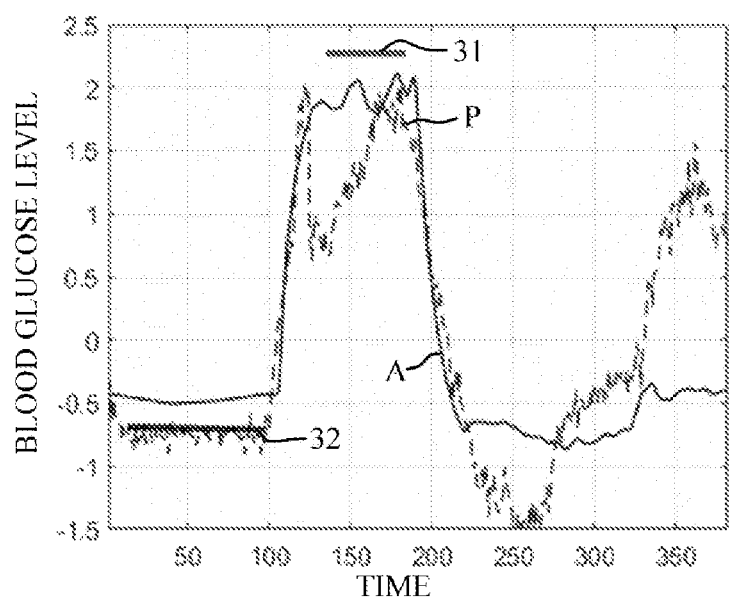

FIGS. 3A to 3C are graphs showing the obtained first feature vector $V_1$ and second feature vector $V_2$. A horizontal axis indicates an inverse number of a wavelength, and a wavenumber indicating a number of waves of a wavelength per unit length; and a vertical axis indicates intensity of the obtained first feature vector $V_1$ and second feature vector $V_2$. FIGS. 3D to 3F are diagrams illustrating an actual blood glucose level A, an estimated blood glucose level P, a first concentration period 31, and a second concentration period 32, according to elapsed time.

The number of principal components is set to 6 in FIGS. 3A and 3D, is set to 13 in FIGS. 3B and 3E, and is set to 25 in FIGS. 3C and 3F.

Based on each set number of principal components, the sensor 110 may obtain the first spectrum and the second spectrum in a first concentration period 31 and a second concentration period 32 as illustrated in FIGS. 3D to 3F. As illustrated herein, the first concentration period is a relatively high concentration period compared to the second concentration period. By obtaining only the first spectrum and the second spectrum as described above, rather than measuring spectra for a long period of time, it is possible to check in real time whether a body component (e.g., blood glucose) is estimated accurately based on the number of principal components which is set in the following manner.

FIGS. 3A to 3C illustrate the first feature vector $V_1$, which is extracted based on the obtained first and second spectra according to each set number of principal components, and the second feature vector $V_2$, which is extracted based on the standard spectrum and the second spectrum according to each set number of principal components. The first feature vector $V_1$ and the second feature vector $V_2$ of FIGS. 3A to 3C correspond to a net analyte spectrum (NAS) vector.

A calculated cosine similarity between the first feature vector and the second feature vector is 0.69 in FIG. 3A, 0.79 in FIG. 3B, and 0.55 in FIG. 3C. That is, in FIG. 3B (the number of principal components being set to 13), directionality of the first feature vector is most similar to directionality of the second feature vector, thus resulting in a highest cosine similarity. In this case, the processor 120 may determine 13 principal components, having the highest cosine similarity, as an optimal number of principal components.

Referring back to FIGS. 3D to 3F, based on the graphs showing the actual blood glucose level A and the estimated blood glucose level P according to elapsed time, it is possible to obtain accuracy in estimating blood glucose according to the set number of principal components. In FIG. 3E in which the number of principal components is set to 13 and the highest cosine similarity is obtained, a highest concordance rate between the actual blood glucose level A and the estimated blood glucose level P is shown; and a predictive evaluation index of blood glucose estimation is 0.64 in FIG. 3D, 0.97 in FIG. 3E, and 0.77 in FIG. 3F, such that it can be seen that the body component may be estimated most accurately in the case of 13 principal components (FIGS. 3B and 3E).

The processor 120 may determine 13 principal components as the optimal number of principal components, and may generate an estimation model based on the optimal number of principal components being 13, by applying at least one analysis algorithm among net analyte signal (NAS), classical least squares (CLS), partial least squares (PLS), Lasso, Neural network, and support vector machine (SVM).

Figure 4:
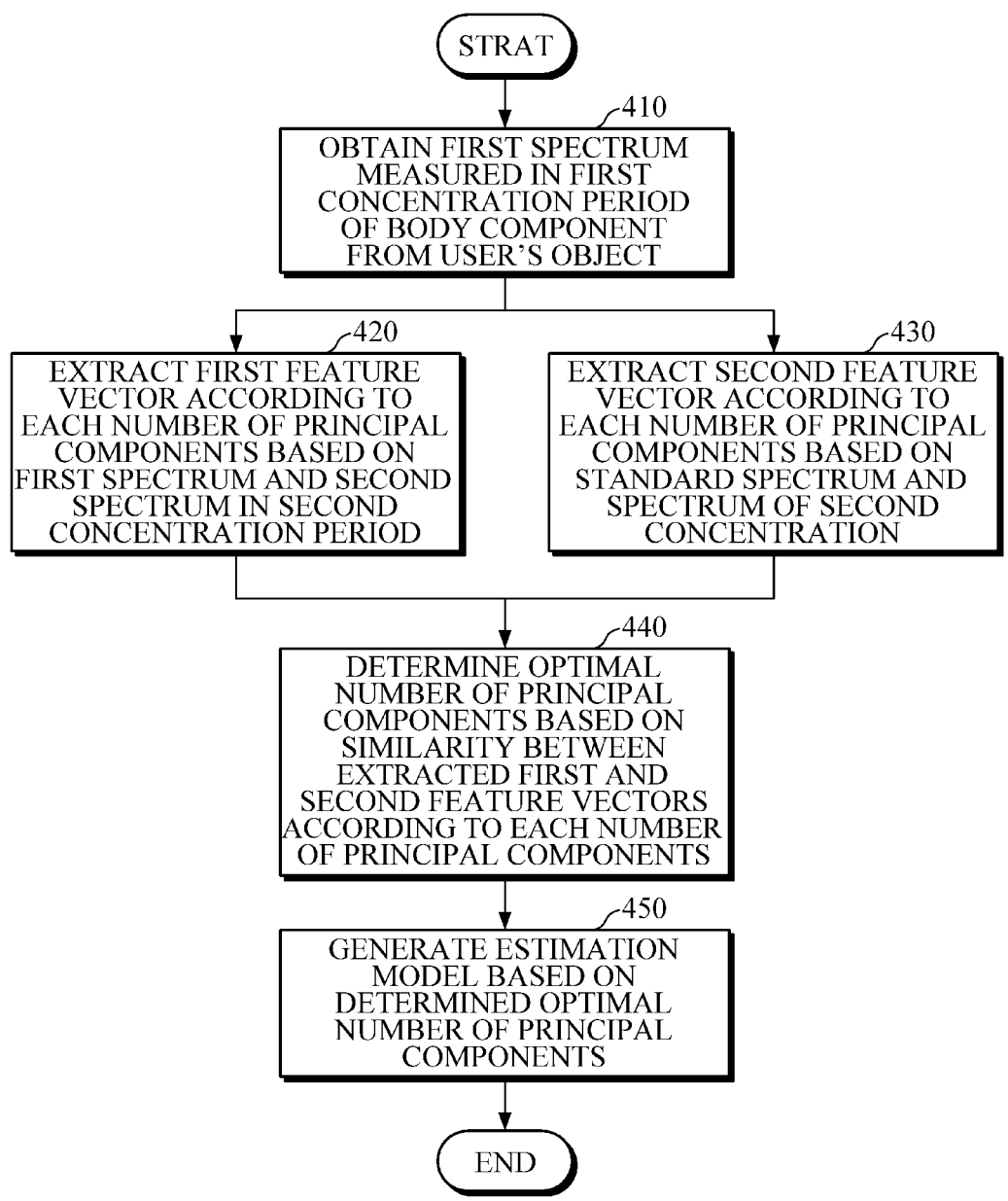
FIG. 4 is a flowchart illustrating a method of calibration for estimating a body component according to an example embodiment of the disclosure.

FIG. 4 is a flowchart illustrating a method of calibration for estimating a body component according to an example embodiment.

The method of FIG. 4 is an example of a method of calibration which is performed by any one of the aforementioned apparatuses 100 and 200 for estimating a body component, and a detailed description of the apparatuses 100 and 200 will be omitted.

First, the apparatus for estimating a body component may obtain a first spectrum measured in a first concentration period of a body component from a user's object in 410.

Then, the apparatus for estimating a body component may extract a first feature vector according to each set number of principal components based on the first spectrum and a second spectrum in a second concentration period in 420. In this case, the first concentration period may refer to a relatively high concentration period compared to the second concentration period. The second spectrum may be measured previously in the second concentration period of the user's body component.

Subsequently, the apparatus for estimating a body component may extract a second feature vector according to each set number of principal components based on a standard spectrum and a spectrum of the second concentration in 430. In this case, the first feature vector and the second feature vector may include a net analyte signal (NAS) vector.

Next, the apparatus for estimating a body component may determine an optimal number of principal components based on a similarity between the extracted first and second feature vectors according to each number of principal components in 440. The similarity includes a cosine similarity. In this case, the apparatus for estimating a body component may determine, as the optimal number, a number of principal components at which a maximum cosine similarity value is obtained between the first feature vector and the second feature vector, among set numbers of principal components.

Then, based on the determined optimal number of principal components, the apparatus for estimating a body component may generate an estimation model for estimating a body component in 450. In this case, based on the determined optimal number of principal components, the apparatus for estimating a body component may generate the estimation model by applying at least one analysis algorithm among net analyte signal (NAS), classical least squares (CLS), partial least squares (PLS), Lasso, Neural network, and support vector machine (SVM).

Figure 5:
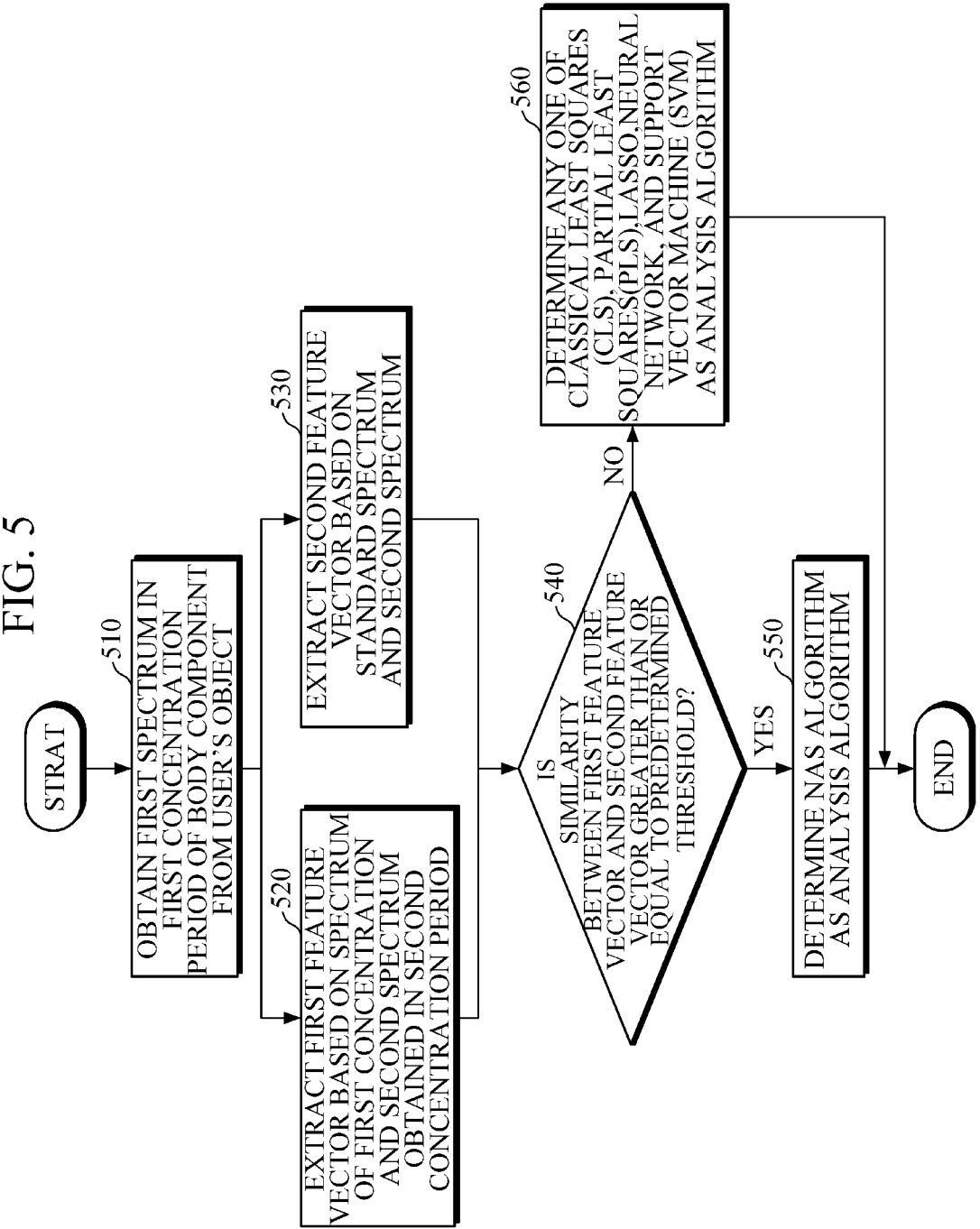
FIG. 5 is a flowchart illustrating a method of calibration for estimating a body component according to another example embodiment of the disclosure.

FIG. 5 is a flowchart illustrating a method of calibration for estimating a body component according to another example embodiment of the disclosure. The method of FIG. 5 is an example of a method of calibration which is performed by any one of the aforementioned apparatuses 100 and 200 for estimating a body component, and a detailed description of the apparatuses 100 and 200 will be omitted.

First, the apparatus for estimating a body component may obtain a first spectrum in a first concentration period of a body component from a user's object in 510.

Then, the apparatus for estimating a body component may extract a first feature vector based on a spectrum of the first concentration and a second spectrum obtained in a second concentration period in 520. The apparatus for estimating a body component may extract a second feature vector based on a standard spectrum and the second spectrum in 530. The first feature vector and the second feature vector may be extracted by using a predetermined number of principal components.

Subsequently, the apparatus for estimating a body component may determine whether a similarity between the first feature vector and the second feature vector is greater than or equal to a predetermined threshold in 540.

Upon determination, if the similarity is greater than or equal to the threshold, the apparatus for estimating a body component may determine, for example, an NAS algorithm as an analysis algorithm in 550; and if the similarity is less than the threshold, the apparatus for estimating a body component may determine any one of classical least squares (CLS), partial least squares (PLS), Lasso, Neural network, and support vector machine (SVM) as an analysis algorithm in 560.

By using the determined analysis algorithm, the apparatus for estimating a body component may generate an estimation model for estimating a body component.

Figure 6A:
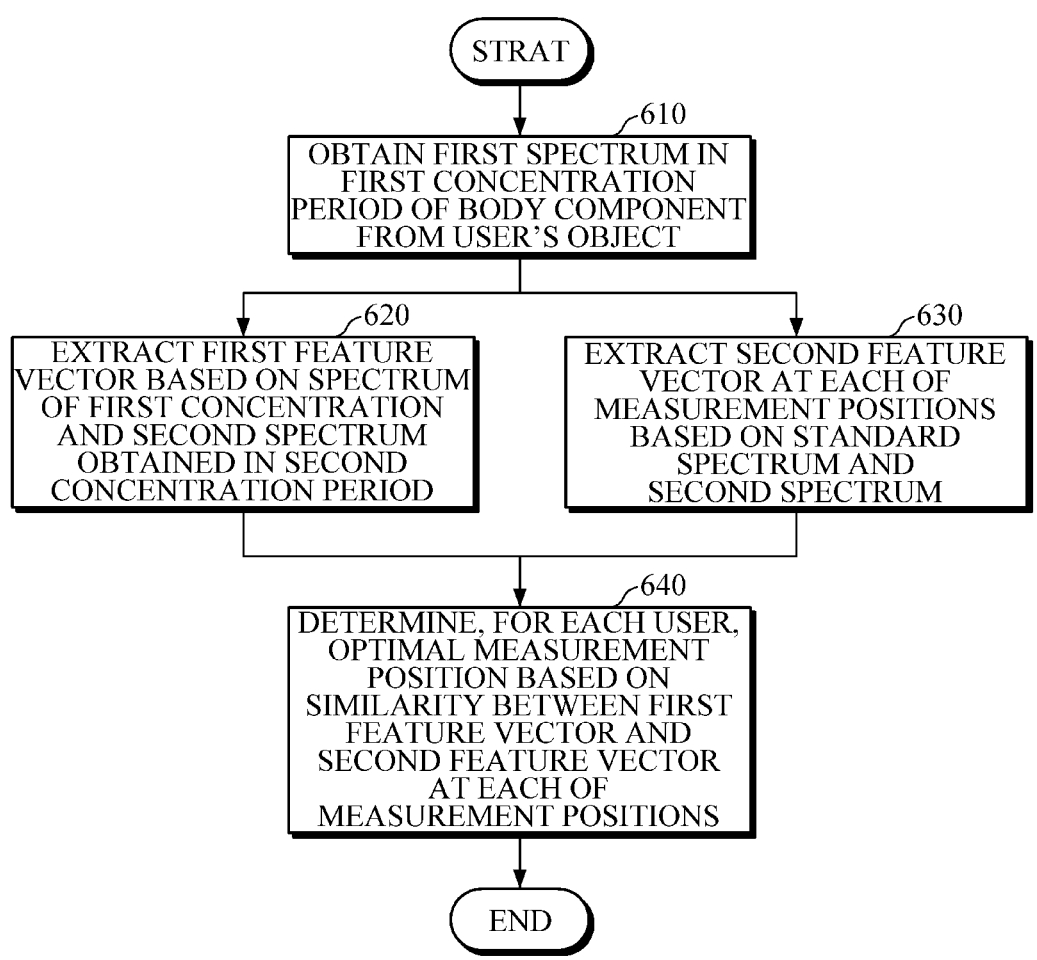
FIG. 6A is a flowchart illustrating a method of calibration for estimating a body component according to yet another example embodiment of the disclosure.

FIG. 6A is a flowchart illustrating a method of calibration for estimating a body component according to yet another example embodiment of the disclosure. The method of FIG. 6A is an example of a method of calibration which is performed by any one of the aforementioned apparatuses 100 and 200 for estimating a body component, and a detailed description of the apparatuses 100 and 200 will be omitted.

First, the apparatus for estimating a body component may obtain a first spectrum in a first concentration period of a body component from a user's object in 610.

Then, the apparatus for estimating a body component may extract a first feature vector at each of a plurality of measurement positions based on a spectrum of the first concentration and a second spectrum obtained in a second concentration period in 620. The apparatus for estimating a body component may extract a second feature vector at each of the plurality of measurement positions based on a standard spectrum and the second spectrum in 630.

Subsequently, the apparatus for estimating a body component may determine, for each user, a database of the plurality of measurement positions and/or an optimal measurement position based on a similarity between the first feature vector and the second feature vector at each of the plurality of measurement positions in 640. In this case, the apparatus for estimating a body component may determine, as the optimal measurement position, a measurement position corresponding to a maximum similarity value among similarities at the respective measurement positions. However, the optimal measurement position is not limited thereto, and the apparatus for estimating a body component may provide a user with the similarities at the respective measurement positions, and then may determine a measurement position, designated by the user, as the optimal measurement position. In addition, with respect to a body component to be estimated, the apparatus for estimating a body component may construct a database, including a list of the plurality of measurement positions, a priority of the plurality of measurement positions, and an optimal measurement position, for each user.

Figure 6B:
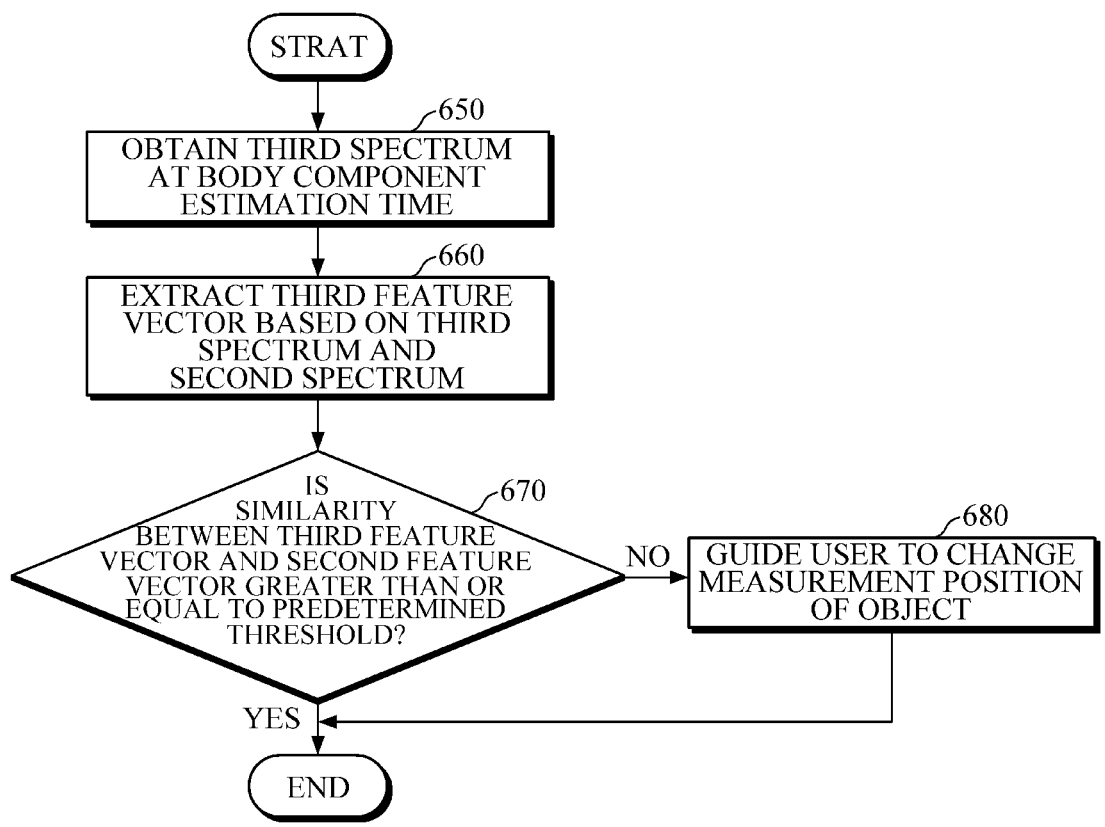
FIG. 6B is a flowchart illustrating a method of estimating a body component according to an example embodiment of the disclosure.

FIG. 6B is a flowchart illustrating a method of estimating a body component according to an example embodiment. The method of FIG. 6B is an example of a method of estimating a body component which is performed by any one of the aforementioned apparatuses 100 and 200 for estimating a body component, and a detailed description of the apparatuses 100 and 200 will be omitted.

First, the apparatus for estimating a body component may obtain a third spectrum at a body component estimation time in 650.

Then, the apparatus for estimating a body component may extract a third feature vector based on the third spectrum and the second spectrum in 660.

Subsequently, the apparatus for estimating a body component may determine whether a similarity between the third feature vector and the second feature vector is greater than or equal to a predetermined threshold in 670.

Upon determination, if the similarity is less than the threshold, the apparatus for estimating a body component may guide a user to change a measurement position of an object in 680. In this case, the apparatus for estimating a body component may guide a user to change a measurement position of the object based on a measurement position database including information on the plurality of measurement positions of each user. The measurement position database may include at least any one of a list of the plurality of measurement positions associated with the body component to be estimated, a priority of the plurality of measurement positions, and an optimal measurement position of each user. In this case, based on the determined priority of the plurality of measurement positions, the apparatus for estimating a body component may guide a measurement position to be changed; or by providing the user with the similarity and priority at each position along with the list of the plurality of measurement positions, the apparatus for estimating a body component may allow the user to designate a measurement position.

Figure 7A:
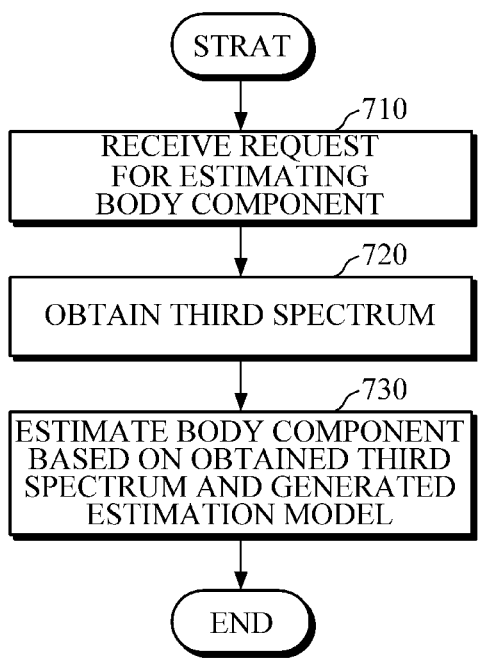
FIG. 7A is a flowchart illustrating a method of estimating a body component according to another example embodiment of the disclosure.

FIG. 7A is a flowchart illustrating a method of estimating a body component according to another example embodiment of the disclosure. The method of FIG. 7A is an example of a method of estimating a body component which is performed by any one of the aforementioned apparatuses 100 and 200 for estimating a body component, and a detailed description of the apparatuses 100 and 200 will be omitted.

First, the apparatus for estimating a body component may receive a request for estimating a body component from a user in 710.

Then, the apparatus for estimating a body component may obtain a third spectrum at a body component estimation time from a user's object in 720.

Subsequently, the apparatus for estimating a body component may estimate a body component based on the obtained third spectrum and the generated estimation model in 730.

Figure 7B:
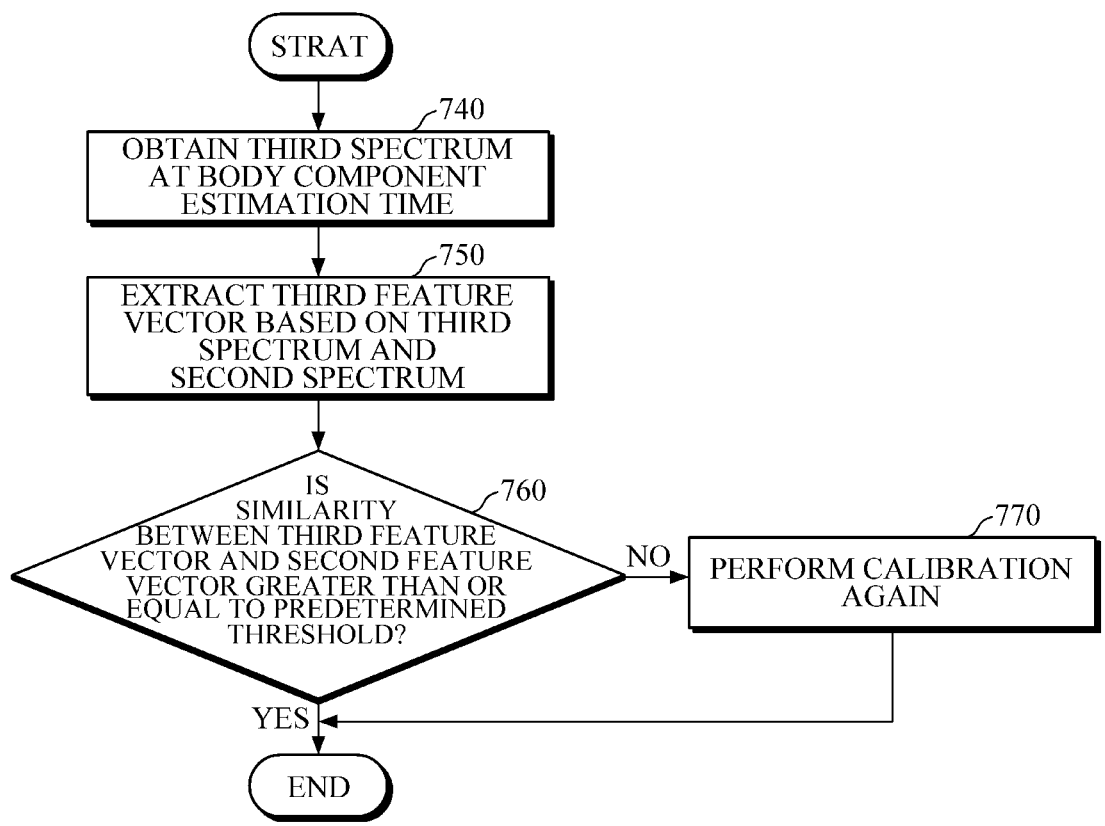
FIG. 7B is a flowchart illustrating a method of determining whether to perform calibration again at a body component estimation time according to another example embodiment of the disclosure.

FIG. 7B is a flowchart illustrating a method of determining whether to perform calibration again at a body component estimation time according to another example embodiment of the disclosure. The method of FIG. 7B is an example of a method of determining which is performed by any one of the aforementioned apparatuses 100 and 200 for estimating a body component, and a detailed description of the apparatuses 100 and 200 will be omitted.

First, the apparatus for estimating a body component may obtain a third spectrum at a body component estimation time from a user's object in 740.

Then, the apparatus for estimating a body component may extract a third feature vector based on the third spectrum and the second spectrum in 750. In this case, the second spectrum may be pre-obtained in a second concentration period at a calibration time.

Subsequently, the apparatus for estimating a body component may determine whether a similarity between the third feature vector and the second feature vector is greater than or equal to a predetermined threshold in 760.

Upon determination, if the similarity is less than the threshold, the apparatus for estimating a body component may perform calibration again in 770. Upon determination, if the similarity is greater than or equal to the threshold, the apparatus for estimating a body component may estimate a body component by using the measured third spectrum.

Figure 8:
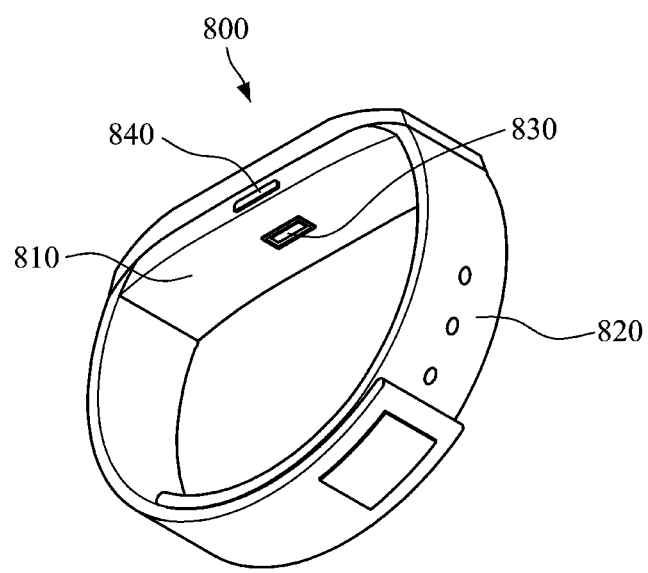
FIG. 8 is a diagram illustrating a wearable device according to an example embodiment of the disclosure.

FIG. 8 is a diagram illustrating a wearable device according to an example embodiment.

Referring to FIG. 8, the wearable device 800 includes a main body 810 and a strap 820.

The strap 820 may include a flexible material. The strap 820 may be connected to both ends of the main body 810, and may be wrapped around a user's wrist so that the main body 810 may be pressed against an upper portion of the wrist. In this case, air may be injected into the strap 820, or the strap 820 may be provided with an air bladder to have elasticity according to a change in pressure applied to the wrist, and may transmit the change in pressure of the wrist to the main body 810.

A battery may be embedded in the main body 810 or the strap 820 to supply power to the wearable device 800. In addition, a sensor part 830 may be mounted on a rear surface of the main body 810. The sensor part 830 may include a light source and a detector as described above.

For example, a processor may be mounted inside the main body 810, and as described above, the processor may perform calibration for estimating a body component by using spectra obtained in different concentration periods, or may estimate a body component by using a body component estimation model obtained by calibration.

For example, the processor may extract the first feature vector based on the first spectrum and the second spectrum, may extract the second feature vector based on the standard spectrum and the second spectrum, and may generate an estimation model for estimating a body component based on a similarity between the first feature vector and the second feature vector.

In another example, by variously setting a number of principal components, the processor may extract the first feature vector and the second feature vector according to each set number of principal components; may determine, as an optimal number, a number of principal components at which a maximum similarity value is obtained between the extracted first and second feature vectors according to each number of principal components; and may generate the estimation model based on the determined optimal number of principal components.

In addition, upon receiving a request for estimating a body component, the processor may control the sensor part 830 to obtain the third spectrum for estimating a body component, and may estimate a body component based on the third spectrum, obtained at an estimation time, and the generated estimation model.

In yet another example, the processor may determine an analysis algorithm based on a similarity between the first feature vector and the second feature vector. In addition, the processor may determine a measurement position of an object based on the similarity between the first feature vector and the second feature vector. A detailed description thereof will be omitted.

Further, a display may be mounted on a front surface of the main body 810. The display may display a body component estimation result, guide information for changing a measurement position of an object, and the like. The display may have a touch screen for receiving touch input.

In addition, the main body 810 may include a storage which stores a variety of reference information for estimating a body component and or processing results of the processor.

In addition, the main body 810 may include a manipulator 840 which is provided on a side surface of the main body 810, and receives a user's control command and transmits the received control command to the processor. The manipulator 840 may have a power button to input a command to turn on/off the wearable device 800.

Moreover, the main body 810 may include a communicator for transmitting and receiving data with an external device. The communicator may communicate with the external device, e.g., a user's smartphone and the like, to transmit and receive various data related to estimating a body component.

Figure 9:
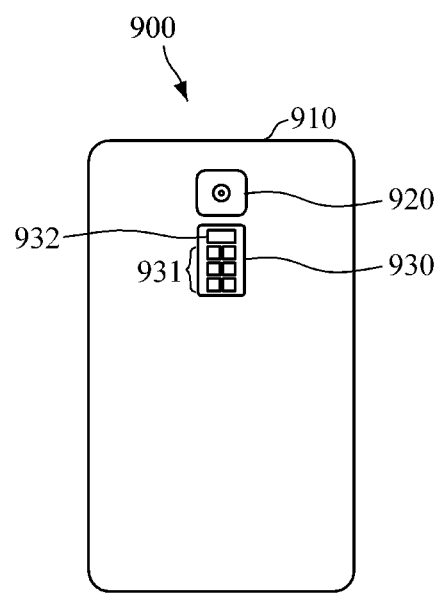
FIG. 9 is a diagram illustrating a smart device according to an example embodiment of the disclosure.

FIG. 9 is a diagram illustrating a smart device according to an example embodiment. In this case, the smart device 900 may include a smartphone, tablet PC, and the like. The smart device 900 may include various embodiments of the aforementioned apparatuses 100 and 200 for estimating a body component.

Referring to FIG. 9, the smart device 900 includes a main body 910 and a sensor part 930 mounted on a rear surface of the main body 910. For example, the sensor part 930 may include a light source 931 and a detector 932. As illustrated in FIG. 9, the sensor part 930 may be mounted on the rear surface of the main body 910, but is not limited thereto. For example, the sensor part 930 may be formed on a fingerprint sensor on the front surface of the smart device, on a portion of a touch panel, or on a power button or a volume button mounted on a side surface or an upper surface of the smart device, and the like.

In addition, a display may be mounted on a front surface of the main body 910. The display may display a variety of information, such as a body component estimation result, guide information for changing a measurement position of an object, and the like.

The main body 910 may include an image sensor 920 as illustrated in FIG. 9. When a user's finger approaches the sensor part 930, the image sensor 920 may capture an image of the finger and may transmit the captured image to the processor. Based on the image of the finger, the processor may identify a relative position of the finger with respect to an actual position of the sensor part 930, and may provide guide information on the relative position of the finger to the user through the display.

As described above, the processor may perform calibration for estimating a body component by using spectra obtained in different concentration periods, or may estimate a body component by using a body component estimation model obtained by calibration. A detailed description thereof will be omitted.

The disclosure may be provided as a computer-readable code written on a computer-readable recording medium. The computer-readable recording medium may be any type of recording device in which data is stored in a computer-readable manner.

Examples of the computer-readable recording medium include a RUM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments for implementing the disclosure may be readily deduced by programmers of ordinary skill in the art to which the disclosure pertains.

While the disclosure has been particularly shown and described with reference to embodiments thereof, it will be understood that various changes in form and details may be made therein without departing from the spirit and scope of the following claims.

What is claimed is:

1. An apparatus for estimating a body component, the apparatus comprising:
a sensor configured to obtain, from an object of a user, a first spectrum in a first concentration period of a body component and a second spectrum in a second concentration period of the body component; and
a processor configured to:
extract a first feature vector based on the first spectrum and the second spectrum;
extract a second feature vector based on a standard spectrum and the second spectrum;
perform first calibration by generating an estimation model for estimating the body component, generation of the estimation model being based on a similarity between the first feature vector and the second feature vector; and
estimate the body component based on a third spectrum, obtained after the first calibration, and the generated estimation model,
wherein the first feature vector and the second feature vector comprise a net analyte signal (NAS) vector, and
wherein the body component comprising at least one of blood glucose, cholesterol, triglyceride, protein, lactate, antioxidant, ethanol, carotenoid, urea, and uric acid.

2. The apparatus of claim 1, wherein the similarity comprises a cosine similarity.

3. The apparatus of claim 1, wherein:
values of the first spectrum obtained by the sensor during the first concentration period is higher than values of the second spectrum obtained by the sensor during the second concentration period; and
the second concentration period includes a period in which the user is in a fasting state.

4. The apparatus of claim 1, wherein by variously setting a number of principal components, the processor is further configured to extract the first feature vector and the second feature vector according to each set number of principal components, determine an optimal number of principal components based on the similarity between the extracted first feature vector and the second feature vector according to each set number of principal components, and generate the estimation model based on the determined optimal number of principal components.

5. The apparatus of claim 4, wherein the processor is further configured to determine, as the optimal number, a set number of principal components at which the similarity between the first feature vector and the second feature vector has a maximum value.

6. The apparatus of claim 4, wherein the processor is further configured to, based on the determined optimal number of principal components, generate the estimation model by applying at least one analysis algorithm of net analyte signal (NAS), classical least squares (CLS), partial least squares (PLS), Lasso, Neural network, and support vector machine (SVM).

7. The apparatus of claim 1, wherein the processor is further configured to extract a third feature vector based on the third spectrum and the second spectrum, and the processor is further configured to, based on a similarity between the third feature vector and the second feature vector being less than a predetermined threshold, perform second calibration.

8. An apparatus for estimating a body component, the apparatus comprising:
a sensor configured to obtain, from an object of a user, a first spectrum in a first concentration period of a body component and a second spectrum in a second concentration period of the body component; and
a processor configured to:
extract a first feature vector based on a spectrum of the first concentration period and the second spectrum;
extract a second feature vector based on a standard spectrum and the second spectrum;
determine at least one of an analysis algorithm or a measurement position of the object based on a similarity between the first feature vector and the second feature vector; and
estimate the body component based on a third spectrum, obtained after the first calibration, and a generated estimation model,
wherein the first feature vector and the second feature vector comprise a net analyte signal (NAS) vector, and
wherein the body component comprising at least one of blood glucose, cholesterol, triglyceride, protein, lactate, antioxidant, ethanol, carotenoid, urea, and uric acid.

9. The apparatus of claim 8, wherein the processor is further configured to, based on the similarity being greater than or equal to a predetermined threshold, determine a net analyte signal (NAS) algorithm as the analysis algorithm, or based on the similarity being less than the predetermined threshold, determine any one of classical least squares (CLS), partial least squares (PLS), Lasso, Neural network, and support vector machine (SVM) as the analysis algorithm.

10. The apparatus of claim 8, wherein the processor is further configured to, based on the similarity being less than a predetermined threshold, control to guide the user to change the measurement position of the object, from which a spectrum is to be obtained.

11. The apparatus of claim 10, wherein the processor is further configured to control to guide the user to change the measurement position of the object, based on a measurement position database including information on a plurality of measurement positions of each user.

12. The apparatus of claim 11, wherein the measurement position database comprises at least any one of a list of a plurality of measurement positions associated with a type of a body component to be estimated, a priority of the plurality of measurement positions, and an optimal measurement position of each user.

13. A method of estimating a body component, the method comprising:
    obtaining, from an object of a user, a first spectrum measured in a first concentration period of a body component and a second spectrum in a second concentration period of the body component;
    extracting a first feature vector based on the first spectrum and the second spectrum;
    extracting a second feature vector based on a standard spectrum and a spectrum of the second spectrum;
    performing first calibration by generating an estimation model for estimating the body component, generation of the estimation model being based on a similarity between the first feature vector and the second feature vector; and
    estimating the body component based on a third spectrum, obtained after the first calibration, and the generated estimation model,
    wherein the first feature vector and the second feature vector comprise a net analyte signal (NAS) vector, and
    wherein the body component comprising at least one of blood glucose, cholesterol, triglyceride, protein, lactate, antioxidant, ethanol, carotenoid, urea, and uric acid.

14. The method of claim 13, further comprising:
    variously setting a number of principal components, and extracting the first feature vector and the second feature vector according to each set number of principal components;
    determining an optimal number of principal components based on the similarity between the extracted first feature vector and the second feature vector according to each set number of principal components; and
    generating the estimation model based on the determined optimal number of principal components.

15. The method of claim 14, wherein the determining the optimal number of principal components comprises determining, as the optimal number, a set number of principal components at which the similarity between the first feature vector and the second feature vector has a maximum value.

16. The method of claim 14, wherein the generating the estimation model based on the determined optimal number of principal components comprises generating the estimation model by applying at least one analysis algorithm of net analyte signal (NAS), classical least squares (CLS), partial least squares (PLS), Lasso, Neural network, and support vector machine (SVM).

17. The method of claim 13, further comprising:
    extracting a third feature vector based on the third spectrum and the second spectrum; and
    based on a similarity between the third feature vector and the second feature vector being less than a predetermined threshold, performing second calibration.

* * * * *